US00PP09671P

United States Patent [19]

Holmes

[11] Patent Number: Plant 9,671

[45] Date of Patent: Oct. 22, 1996

[54] ST. AUGUSTINEGRASS NAMED 'W-1'

[75] Inventor: James M. Holmes, Crystal Lake, Ill.

[73] Assignee: Warren's Turf Group, Inc., Crystal Lake, Ill.

[21] Appl. No.: 393,440

[22] Filed: Feb. 23, 1995

[51] Int. Cl.[6] ..... A01H 5/00

[52] U.S. Cl. ..... Plt./90.1

[58] Field of Search ..... Plt./90.1

[56] References Cited

U.S. PATENT DOCUMENTS

| | | | |
|---|---|---|---|
| P.P. 2,863 | 2/1969 | Long | Plt./90.1 |
| P.P. 2,864 | 2/1969 | Long | Plt./90.1 |
| P.P. 3,180 | 5/1972 | Gruis et al. | Plt./90.1 |
| P.P. 3,491 | 2/1974 | Garrett et al. | Plt./90.1 |
| P.P. 3,681 | 2/1975 | Gruis et al. | Plt./90.1 |
| P.P. 3,698 | 4/1975 | Gruis et al. | Plt./90.1 |
| P.P. 3,834 | 3/1976 | Garrett | Plt./90.1 |
| P.P. 4,097 | 9/1977 | Gruis et al. | Plt./90.1 |
| P.P. 6,126 | 3/1988 | Riordan | Plt./90.1 |
| P.P. 6,372 | 11/1988 | Mixson et al. | Plt./90.1 |
| P.P. 6,921 | 7/1989 | Mixson et al. | Plt./90.1 |
| P.P. 6,922 | 7/1989 | Mixson et al. | Plt./90.1 |
| P.P. 7,699 | 10/1991 | Busey | Plt./90.1 |
| P.P. 7,852 | 4/1992 | Busey | Plt./90.1 |

*Primary Examiner*—James R. Feyrer

*Attorney, Agent, or Firm*—Klarquist, Sparkman Campbell Leigh & Whinston, LLP

[57] ABSTRACT

An asexually reproduced variety of perennial St. Augustinegrass with a unique combination of characters including white stigmas, yellow anthers, an absence of leaf hairs, floret number per raceme, raceme length, leaf length, and internode length, having good turf performance, good winter hardiness, and a distinct DNA fingerprint.

3 Drawing Sheets

BACKGROUND OF THE INVENTION

This invention relates to a new and distinct perennial St. Augustinegrass cultivar, tested as W-1, that was discovered by the inventor in the State of California. It was identified as a clone superior in quality (density and uniformity) to the surrounding California Common St. Augustinegrass grown on a sod farm in Winchester, Calif. California Common was the only St. Augustinegrass on the farm or in the immediate area. W-1 is a high quality, stoloniferous turf with good winter hardiness for use as a lawn or turf wherever St. Augustinegrass is adapted, with improved winter survival in the northern areas of St. Augustinegrass adaptation with the coldest winters, such as Dallas-Ft. Worth, Tex.

BRIEF DESCRIPTIONS OF THE ILLUSTRATIONS

FIGS. 1 and 2 are DNA fingerprints of St. Augustinegrass varieties. The DNA fingerprints were produced by polymerase chain reaction using random primers, illustrating W-1 is different from Seville and Raleigh.

DETAILED DESCRIPTION OF THE PLANT

Figure 1:
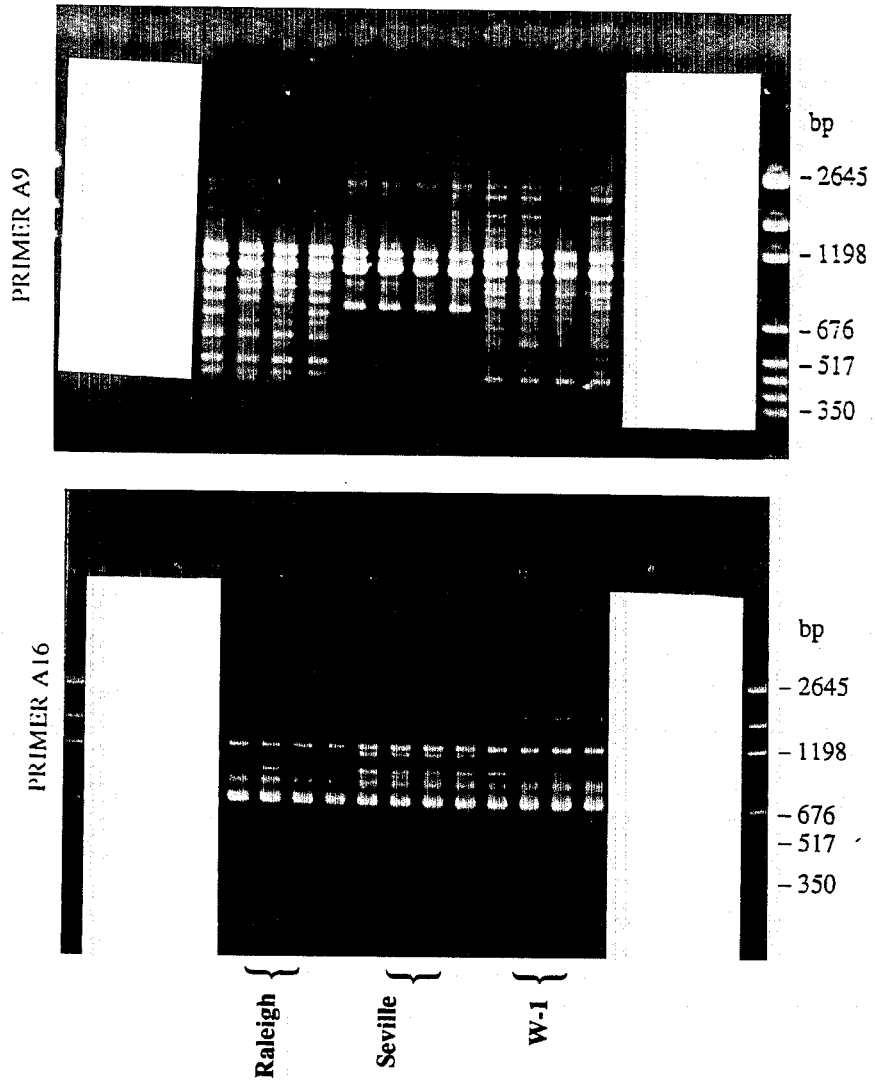

W-1 was characterized in greenhouse and field conditions. W-1 is a unique variety of St. Augustinegrass [*Stenotaphrum secundatum* (Walt). Kuntze] discovered under cultivated, mowed turf conditions at the sod farm described above. W-1 was identified as higher in density and uniformity from the surrounding California Common St. Augustinegrass. W-1 was propagated by cutting of stolons, rooting them in soil, and planting of the rooted stolons to provide planting stock for studying performance and for comparisons with commercial varieties. W-1 remained stable in both performance and morphological characters after propagation. W-1 has been propagated by sod, plugs, and stolons. No seedling establishment from W-1 has been noticed in either greenhouse or field plantings, suggesting lack of sexual reproduction.

W-1 distinguished from other varieties of St. Augustinegrass by the combination of characters of white stigmas, yelow anthers, floret number per raceme, raceme length, leaf length, intermode length and diameter, spikelet length, leaf and internode color, and lack of leaf hairs. W-1 shows a distinct DNA fingerprint. W-1 is closest in appearance and performance to Raleigh St. Augustinegrass.

The creeping stolons of W-1 are dorsiventrally compressed and root adventitiously at the nodes. W-1 lacks rhizomes. Color notations of plant tissues were based on the *Munsell Color Charts for Plant Tissues,* Munsell Color, Baltimore, Md., 1977. Color notations are affected by light quality and fertility and general growth of the plants. The internode color of W-1 is 7.5 GY 5/6, with Raleigh, held under the same growth conditions, at 7.5 GY 5/6. W-1 has a distinct lack of purple color in the stolons, in contrast to many St. Augustinegrasses. Leaf blades of W-1 are folded in the bud, contracted at the base, and obtuse at the tip. Leaf blade lengths vary by growing conditions, but the third youngest unmowed leaf on a stolon in August, Buckholdts, Tex. ranged from 16 to 85 mm with a mean of 34.9 mm of for 15 leaves. There is an absence of hairs on the leaf blades of W-1. Measured under greenhouse conditions in Jul. 1994, the genetic, adaxial leaf color of W-1 is 5 GY 6/6, with Raleigh having a color of 5 GY 5/8. Measured under greenhouse conditions in October 1995, the genetic, adaxial leaf color of W-1 is 7.5 GY 5/6, with Raleigh having a color of 7.5 GY 4/6.

The ligule of W-1 is a line of short hairs, approximately 2 mm in length. The leaf sheaths are laterally compressed and are approximately 32.5 mm in length (Table 1), shorter than Raleigh at a mean of 40.9. Using ratios established in U.S. Plant Pat. No. 6,921, the ratio of leaf sheaths of Raleigh:California Common=1.68 (3.7/2.2). By comparison from data in Table 1, W-1 has a longer leaf sheath than California Common (Raleigh:W-b 1leaf sheath ratio=1.25 (40.9/32.5).

The flag leaf width of W-1 is 6.6 mm, with Raleigh having a mean of 7.06 mm (Table 2). W-1 has white stigmas and yellow anthers, undistinguished in color from other plants of the species (Table 3). The floral region of W-1 consists of spikelets partially embedded in a flattened and thickened rachis of a short, unilateral spicate inflorescence with a raceme length of 55 to 70 mm (Table 4). W-1 has a mean of 28 spikelets per raceme, which trends to be a lower number of spikelets than Raleigh, and more than Seville (Table 4). The mean spikelet length of W-1 is 3.8 mm, with Raleigh having a mean of 4.23, measured under the same growth conditions. The spikelets of W-1 are awnless.

The mean stolon internode diameter of W-1 is 2.29×3.1 mm, less than Raleigh with a stolon diameter of 3.1×3.5 mm. By U.S. Plant Pat. No. 6,921, California Common has an internode diameter of 2.4×2.0 mm, and Raleigh with an internode diameter of 3.2×2.5 mm. W-1 has a mean internode length of6.45 cm (Table 5), shorter than Raleigh with a mean of 7.8 cm, and longer than Seville with a mean of 4.2 cm.

The chromosome number of W-1 is 18.

Quality in turf performance may be defined as a combination of characters of color, density, uniformity, and leaf texture. Density is defined as the number of leaves and tillers per unit area. Uniformity is defined as freedom from weeds or diseases. W-1 shows high quality turf performance in field trails in Buckholts, Tex. (Tables 6, 7, and 8). In these trails, W-1 showed quality as finer leaf texture than Raleigh, tiller density higher than Raleigh, good uniformity, and acceptable turf color. W-1 has good turf performance when mowed at 5 cm mowing height, with a rotary mower. W-1 is vigorous in establishing a turf cover, as indicated in the growth from a 22.5% cover to 73.8% in an approximate 6-month period (Table 8).

The high quality performance of W-1 may be directly related to the high tiller density which competes with weeds, and the superior winter hardiness (tested as survival in Buckholts, Tex., Table 8). Thatch measurements taken from replicated trails located at Buckholts, Tex. during August and October 1994 showed no significant difference in thatch depth between W-1 and Raleigh of Texas Common. Thatch, defined as the tightly intermingled layer of dead and living stems and roots would be excessively different only if the rate of accumulation exceed the rate of decomposition. W-1's lack of high thatch accumulation is a positive attribute, and in comparison to Raleigh could be accounted for by increased tiller production but with moderate leaf lengths and widths. Raleigh has fewer tillers but longer leaves, so the two varieties may have dissimilar but compensating factors.

W-1 has good winter hardiness as illustrated by percent cover after the 1993–94 winter in Buckholts, Tex., was not different from Raleigh, and was superior to both Seville and Texas Common (Table 8), A lower percent cover after the winter of 1993–94 would have indicated more susceptibility to frost and winter damage. Observations of W-1 during the 194–95 winter at Buckholts, Tex. showed winter hardiness not different from Raleigh. Personal observation of turf performance in Buckholts, Tex. indicates moisture stress resistance similar to Raleigh. W-1 has shown moderate susceptibility to gray leaf spot in the Buckholts, Tex. trials. The shade tolerance of W-1 has not been tested.

Figure 2:
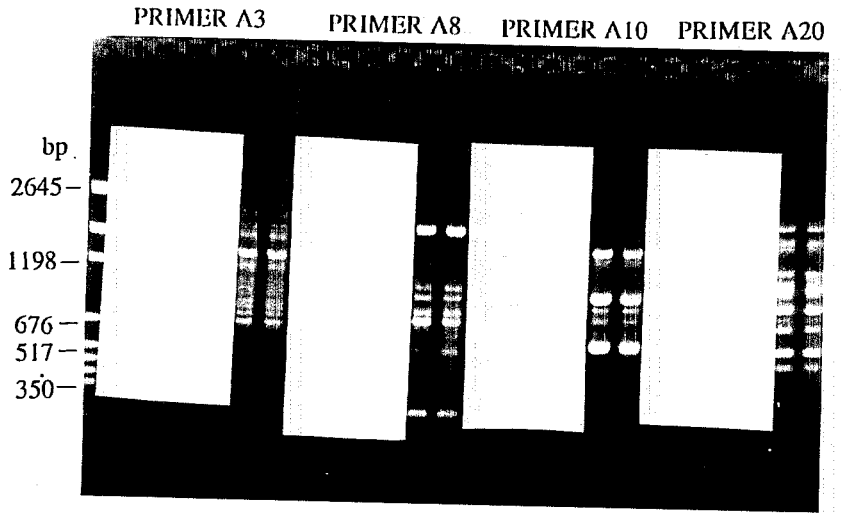
Figure 3:
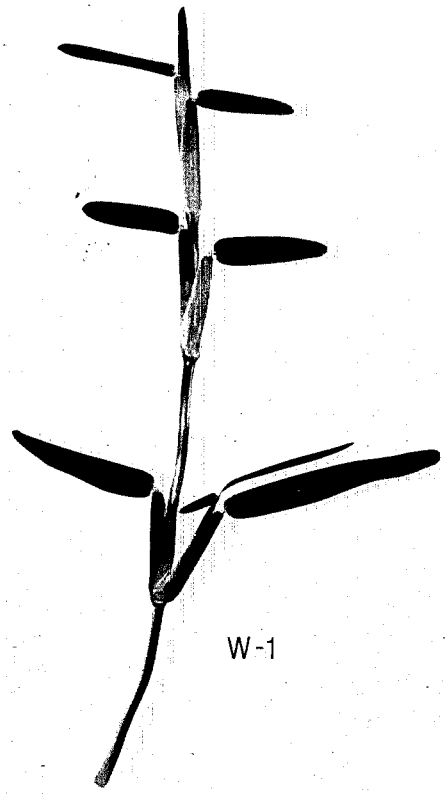
FIG. 3 is a photograph of a vegetative stolon of W-1.
Figure 5:
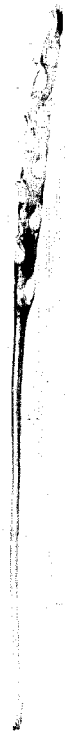
FIG. 5 is a photograph of the inflorescence of W-1.
Figure 4:
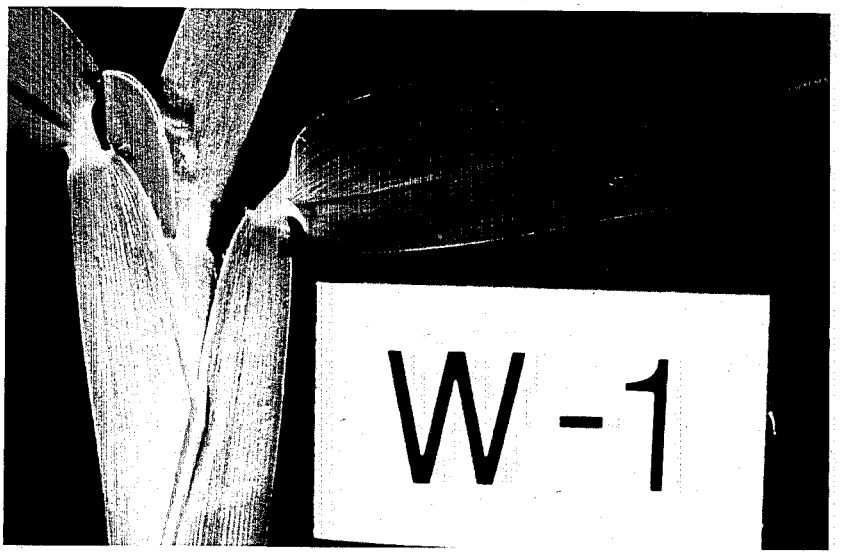
FIG. 4 is a photograph of the leaf blade and ligule of W-1.

With the presence of white stigmas, yellow anthers, and an absence of leaf hairs, W-1 is distinguished from all patented St. Augustinegrasses except #141, 6-72-99 (Delmar), and 6-72-182 (Tables 3, 3a). W-1 exhibits more florets per raceme than Seville (Table 4), is not different from number of florets per raceme than Raleigh, but has a shorter raceme length than Raleigh. W-1 has a flag leaf sheath longer than Seville (Table 1); Seville has a flag leaf sheath longer than 6-72-182 (U.S. Plant Pat. No. 6,922). W-1 has a raceme averaging 67.3 mm (Table 4). Delmar has a spike 93 mm in length (U.S. Plant Pat. No. 6,372), with #141 having an average length of 8.97 cm (U.S. Plant Pat. No. 3,834), both longer than W-1. W-1 has a longer leaf length (Table 2) and longer internodes (Table 5) than #141 (U.S. Plant Pat. No. 3,834). W-1 shows a distinctly different DNA from Seville and Raleigh using PCR DNA fingerprints (FIGS. 1 and 2).

TABLE 1

Morphological comparisons of W-1 and commercial St. Augustinegrass varieties measured from plants maintained in greenhouse pots.

| Variety | Sheath Length[1] mm | Sheath Length[2] mm | Sheath Length[3] mm | Leaf Width[3] mm |
|---|---|---|---|---|
| W-1 | 40.4b | 33.5a | 23.6b | 6.3c |
| Raleigh | 52.9a | 36.3a | 33.6a | 8.9a |
| Seville | 35.2b | 22.4c | 17.6c | 5.8c |

[1]Measured on flag leaf sheaths, Sept. 1993; Mean separation by General Linear Models.
[2]Measured on flag leaf sheaths, Oct. 1994; Mean separation by Waller/Duncan tests.
[3]Measured on 3rd youngest leaf, Sept. 1993; Mean separation by Waller/Duncan tests.

TABLE 2

Comparisons of W-1 and other St. Augustinegrass flag leaf widths and lengths.

| Variety | Flag Leaf Width[1] mm | Flag Leaf Width[2] mm | Flag Leaf Width[3] mm | Flag Leaf Length[4] mm |
|---|---|---|---|---|
| W-1 | 4.8ab | 8.0a | 7.0a | 18.5a |
| Raleigh | 5.2a | 7.9a | 8.1a | 19.8a |
| Tx. Common | 4.2b | . | . | . |
| Seville | . | 5.9b | 5.1b | 9.9b |

[1]Measured July 1993 from replicated field trials, Buckholts, TX, with mean separation by General Linear Models.
[2]Measured July 1994 on greenhouse planted material with mean separation by Waller/Duncan tests.
[3]Measured Oct. 1994 on greenhouse planted material with mean separation by Waller/Duncan tests.
[4]Measured Oct. 1994 on greenhouse planted material with mean separation by Waller/Duncan tests.

TABLE 3

Stigma color, anther color, and presence of leaf hairs on St. Augustinegrass varieties from plants maintained in greenhouse pots, July 1994.

| Variety | Stigma color | Anther color | Leaf hairs |
|---|---|---|---|
| W-1 | white | yellow | absent |
| Raleigh | white | yellow | absent |
| Seville | purple | yellow | absent |

TABLE 3a

Stigma color, anther color, and leaf hairs of St. Augustinegrasses as listed in US Plant Patents.

| Variety | Stigma Color | Anther Color | Leaf Hairs | U.S. Patent |
|---|---|---|---|---|
| Ea 611081 | Purple | . | . | 2,863 |
| Ea 6416 | Purple | . | . | 2,864 |
| Ea 673 | Purple | . | . | 3,180 |
| #4875 | Purple* | . | . | 3,491 |
| 73176 | Purple | . | . | 3,681 |
| 45176 | Purple | . | . | 3,698 |
| # 141 | White | . | . | 3,834 |
| 615866 (Seville) | Purple | . | . | 4,097 |
| PS-247 | Purple | Light purple | . | 6,126 |
| 6-72-99 (Delmar) | White | Yellow | . | 6,372 |
| 6-72-182 | White | Yellow | . | 6,921 |
| 6-72-130 | Purple | Purple | . | 6,922 |
| FX-33 | Purple | Orange Yellow | Many | 7,699 |
| FX-10 | 5RP 3/10 | 10YR 7/10 | Present | 7,852 |

*With white filaments

TABLE 4

Morphological comparisons of W-1 and other commercial St. Augustinegrass varieties measured from plants maintained in greenhouse pots.

| Variety | Floret[1] # | Floret[2] # | Floret[3] # | Raceme Length[1] mm | Raceme Length[2] mm | Raceme Length[3] mm |
|---|---|---|---|---|---|---|
| W-1 | 33.8a | 29.8a | 21.5a | 69.8b | 64.7b | 55.7a |
| Raleigh | 34.2a | 30.1a | 19.2a | 93.3a | 76.5a | 59.6a |
| Seville | 24.1b | 23.7b | 13.0b | 67.8b | 61.3c | 41.7b |

[1]Measured Sept. 1993; Mean separation by General Linear Models.
[2]Measured July 1994; Mean separation by Waller/Duncan tests.
[3]Measured October 1994; Mean separation by Waller/Duncan tests.

TABLE 5

Stolon internode lengths of W-1 and commercial St. Augustinegrass varieties measured from plants maintained in greenhouse pots.

| Variety | Internode 2–3 cm | Internode 3–4 cm |
|---|---|---|
| W-1 | 6.4b[1] | 6.5b |
| Raleigh | 8.1a | 7.5a |
| Seville | 4.2c | 4.2c |

[1]Measured 2 October 1994 with mean separation by Waller/Duncan tests.

TABLE 6

Quality ratings of W-1 and other commercial St. Augustinegrass varieties established as sod in replicated field trials, Buckholts, TX.

| | Date | | | | |
|---|---|---|---|---|---|
| Variety | 26 Jul 93 | 17 Aug 93 | 11 Oct 93 | 17 Oct 94 | 4 July 94 |
| | Quality Ratings[1] | | | | % Cover[3] |
| W-1 | 7.3a[2] | 6.5a | 6.8a | 4.8a | 29.0a |
| Raleigh | 5.9b | 5.5a | 5.4b | 5.0a | 37.0a |
| Tx. Com. | 3.4c | 3.0b | 3.4c | 2.0b | 1.2b |

[1]Ratings made on a scale of 1–9 with 9 = best.

TABLE 6-continued

Quality ratings of W-1 and other commercial St. Augustinegrass varieties established as sod in replicated field trials, Buckholts, TX.

| | Date | | | | |
|---|---|---|---|---|---|
| Variety | 26 Jul 93 | 17 Aug 93 | 11 Oct 93 | 17 Oct 94 | 4 July 94 |
| | Quality Ratings[1] | | | | % Cover[3] |

[2]Mean separation by General Linear Models on 26 July, Waller/Duncan on 17 August and 11 October 1993, and 17 October 1994.
[3]Mean separation by Waller/Duncan.

TABLE 7

Density ratings of W-1 and other commercial St. Augustinegrass varieties established as sod in replicated field trials, Buckholts, TX.

| | Date | | |
|---|---|---|---|
| Variety | 26 July 93 | 17 Aug 93 | 11 Oct 93 |
| | Density Ratings[1] | | |
| W-1 | 6.6a[2] | 7.0a | 6.8a |
| Raleigh | 4.6b | 5.2b | 5.2b |
| Tx. Common | 2.8c | 3.8c | 4.0c |

[1]Density rated on a scale of 1–9 with 9 = best.
[2]Mean separation by Waller/Duncan.

TABLE 7a

Mean tiller number per four-inch diameter core of W-1 and other commercial St. Augustinegrass varieties established as sod in replicated trials, Buckholts, TX.

| Variety | Tiller number | |
|---|---|---|
| W-1 | 19.7a[1] | 25.7a[2] |
| Raleigh | 17.0a | 19.7ab |
| Tx. Com. | 8.7b | 16.5b |

[1]Mean of two cores per plot used for analysis purposes, measured 8 Sept. 1994. Mean separation by Waller/Duncan tests.
[2]Mean of two cores per plot used for analysis purposes, measured 17 October 1994. Mean separation by Waller/Duncan.

TABLE 8

Percent plot cover and density ratings of W-1 and other commercial St. Augustinegrass varieties established July 1993 from plugs in replicated trials at Buckholts, TX. Percent cover relates to winter survival as measured on 22 April 1994.

| | Date | | |
|---|---|---|---|
| Variety | 22 Apr 94 | 17 Oct 94 | 17 Oct 94 |
| | % Cover | | Density Rating |
| W-1 | 22.5a[1] | 73.8a | 6.0a[2] |
| Raleigh | 17.5a | 80.0a | 5.5a |
| Seville | 3.3b | 52.5a | 4.0a |
| Tx. Com. | 1.3b | 3.0b | 0.3b |

[1]Mean separation by Waller/Duncan.
[2]Rated on a scale of 1–9 with 9 = most dense, with mean separation by Waller/Duncan.

DETAILED SUMMARY OF DNA FINGERPRINT ANALYSIS

Dr. Lin Wu, Univ. California—Davis, performed the DNA fingerprint analysis. The St. Augustinegrass DNA fingerprints were W-1, Seville, and Raleigh. the DNA fingerprints were produced by polymerase chain reaction using random primers. The four DNA fingerprint profiles of each variety produced by the primers A9 and A16 from the left to right are the DNA profiles of the two duplicate DNA extractions extracted from the leaf tissue of the vegetatively propagated clones. The results of the DNA fingerprint analysis are summarized:

1 W-1 is different from Raleigh by Primer A9 and A16.

2. W-1 is different from Seville by Primer A9 and A16.

I claim:

1. A new and distinct cultivar of an asexually reproduced St. Augustinegrass plant, as shown and described, with a unique combination of characters including white stigmas, yellow anthers, an absence of leaf hairs, floret number per raceme, raceme length, leaf length, and intermode length, having good turf performance, good winter hardiness, and a distinct DNA fingerprint.

* * * * *

W-1